United States Patent
Perraud et al.

(10) Patent No.: US 10,258,787 B2
(45) Date of Patent: Apr. 16, 2019

(54) CUTANEOUS MEDICAL DEVICE COMPRISING A MAIN PART AND INCLUDING A BASE AND A REMOVABLE ELECTRODE

(71) Applicant: COMMISSARIAT A L'ENERGIE ATOMIQUE ET AUX ENERGIES ALTERNATIVES, Paris (FR)

(72) Inventors: Simon Perraud, Bandol (FR); Nicolas Karst, Folkling (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 15/309,528

(22) PCT Filed: May 19, 2015

(86) PCT No.: PCT/IB2015/053680
§ 371 (c)(1),
(2) Date: Nov. 8, 2016

(87) PCT Pub. No.: WO2015/177725
PCT Pub. Date: Nov. 26, 2015

(65) Prior Publication Data
US 2017/0151427 A1    Jun. 1, 2017

(30) Foreign Application Priority Data

May 19, 2014   (FR) ..................................... 14 54456

(51) Int. Cl.
*A61N 1/04*      (2006.01)
*A61N 1/32*      (2006.01)
*A61N 1/36*      (2006.01)

(52) U.S. Cl.
CPC ......... *A61N 1/0492* (2013.01); *A61N 1/0452* (2013.01); *A61N 1/0456* (2013.01); *A61N 1/32* (2013.01); *A61N 1/36014* (2013.01)

(58) Field of Classification Search
CPC .. A61N 1/0492; A61N 1/0452; A61N 1/0456; A61N 1/36014
See application file for complete search history.

(56) References Cited

U.S. PATENT DOCUMENTS

| | | | |
|---|---|---|---|
| 5,562,607 A * | 10/1996 | Gyory .................. | A61N 1/0436 439/188 |
| 2011/0288393 A1 * | 11/2011 | Holzhacker ........ | A61B 5/04085 600/391 |

(Continued)

FOREIGN PATENT DOCUMENTS

| EP | 1106204 A1 | 6/2001 |
|---|---|---|
| FR | 2961340 A1 | 12/2011 |
| WO | 2013/107635 A2 | 7/2013 |

OTHER PUBLICATIONS

Rapport de Recherche Preliminaire mailed Oct. 23, 2014, issued in priority French Application No. 1454456, filed May 19, 2014, 1 page.

(Continued)

*Primary Examiner* — Rex R Holmes
(74) *Attorney, Agent, or Firm* — Christensen O'Connor Johnson Kindness PLLC

(57) ABSTRACT

A cutaneous medical device having a main part containing an electrical energy source that can generate an electric current and electronic components that form part of an electric circuit; and at least one removable cutaneous electrode comprising an electric plug. The electrode is intended to be in electric contact with a user. The electrode also includes at least one base which is positioned on a first face (Continued)

Figure 1A:
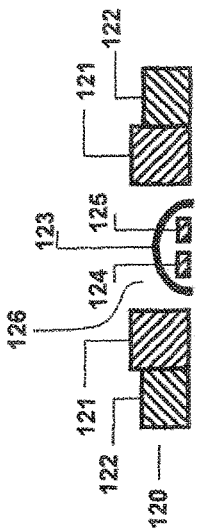

of the main part and can be electrically connected to the at least one removable cutaneous electrode.

16 Claims, 6 Drawing Sheets

(56) References Cited

U.S. PATENT DOCUMENTS

| | | |
|---|---|---|
| 2011/0303520 A1 | 12/2011 | Burnel et al. |
| 2012/0253263 A1 | 10/2012 | Netzel et al. |
| 2013/0046212 A1 | 2/2013 | Nichols |
| 2013/0281914 A1* | 10/2013 | Yaegashi ............... A61N 1/044 604/20 |
| 2015/0005681 A1 | 1/2015 | Gimelli et al. |

OTHER PUBLICATIONS

International Search Report dated Sep. 22, 2015, issued in corresponding International Application No. PCT/IB2015/053680, filed May 19, 2015, 3 pages.

Written Opinion of the International Searching Authority dated Sep. 22, 2015, issued in corresponding International Application No. PCT/IB2015/053680, filed May 19, 2015, 7 pages.

Written Opinion of the International Searching Authority dated Sep. 22, 2015, issued in corresponding International Application No. PCT/IB2015/053680, filed May 19, 2015, 8 pages.

International Preliminary Report on Patentability dated Nov. 22, 2016, issued in corresponding International Application No. PCT/IB2015/053680, filed May 19, 2015, 1 page.

\* cited by examiner

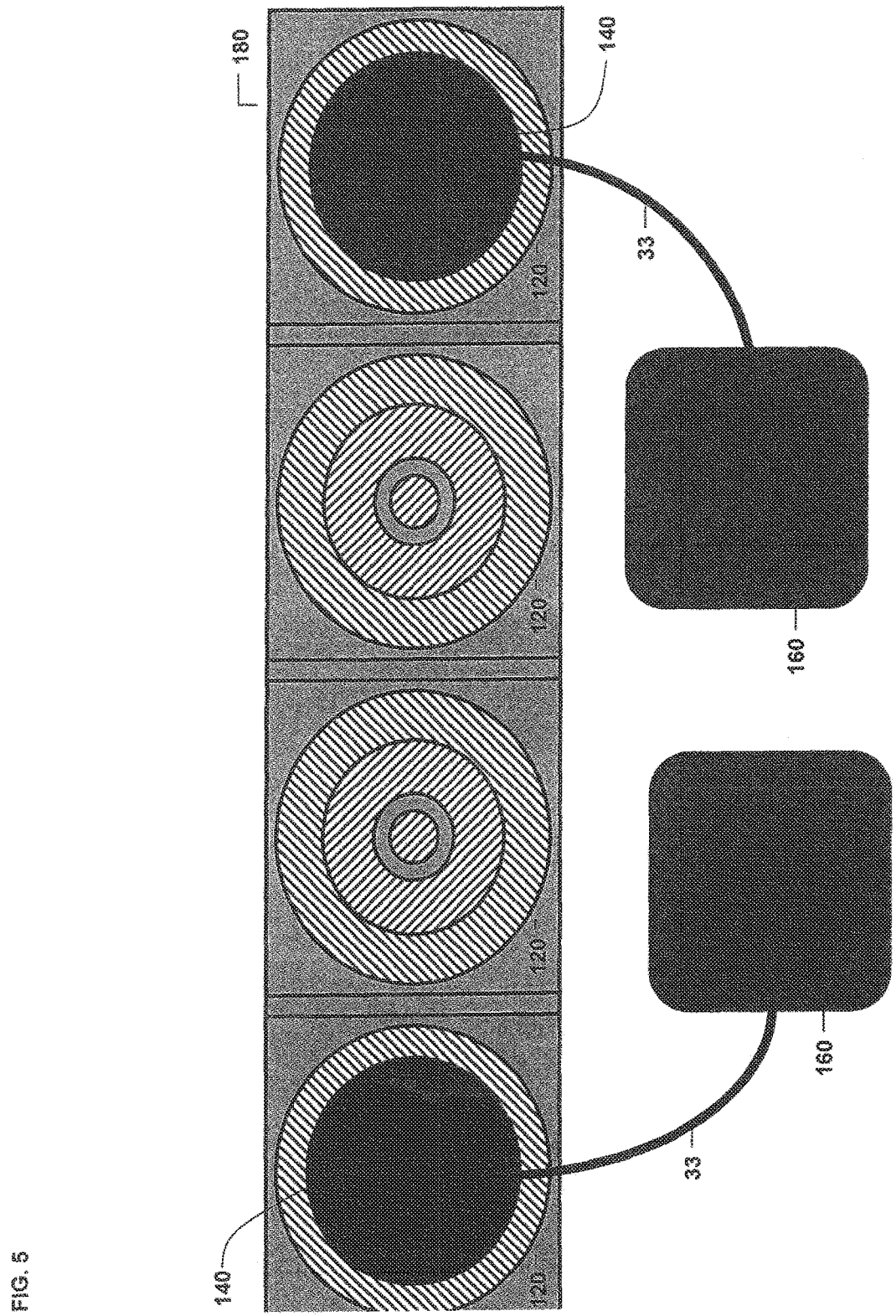

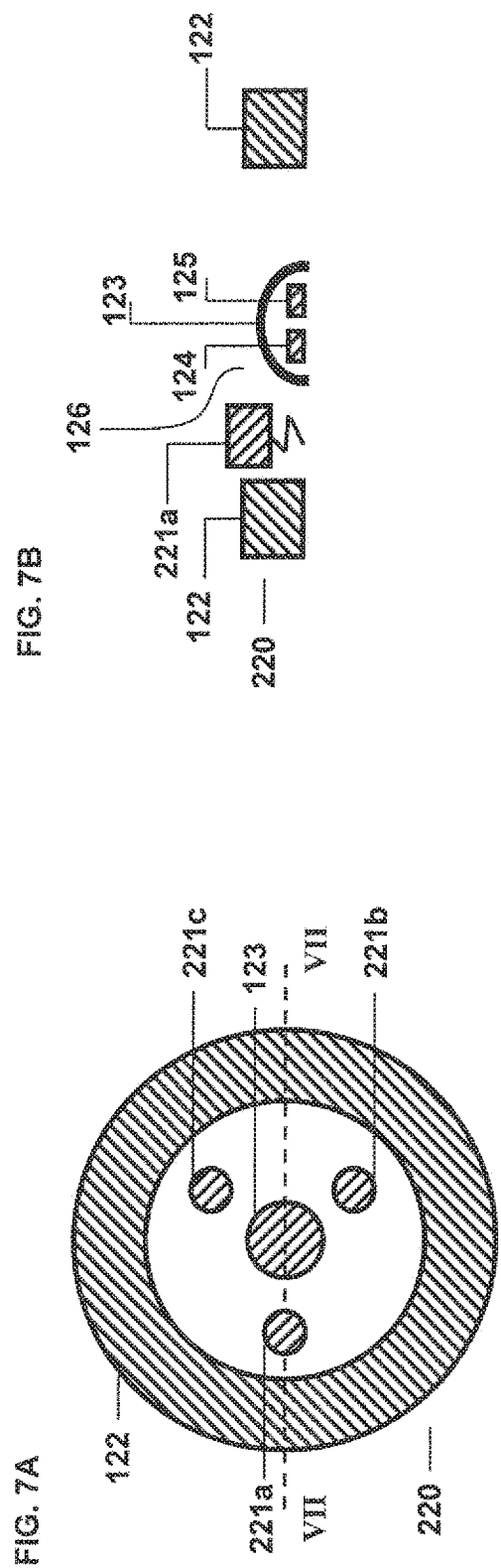

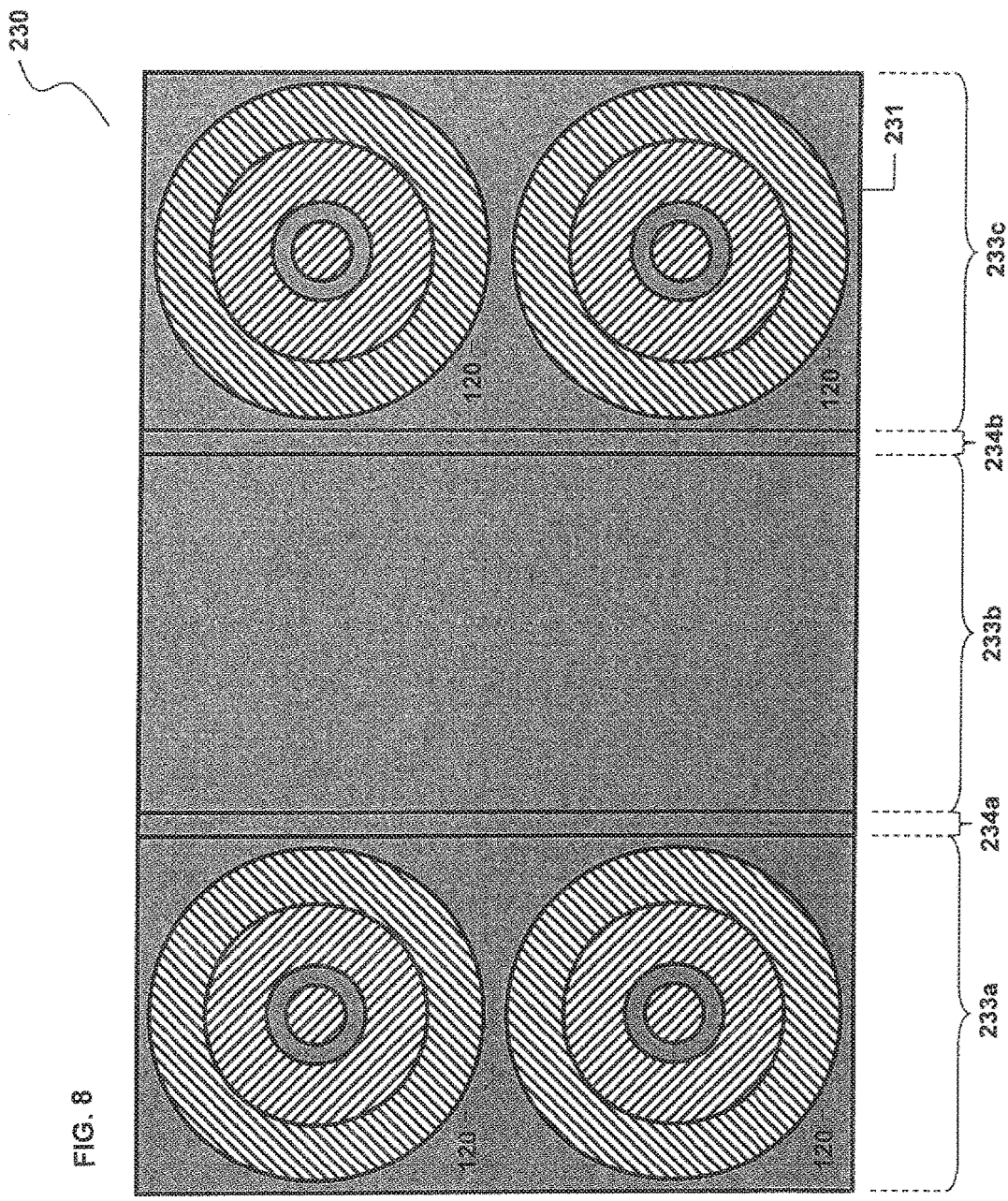

CUTANEOUS MEDICAL DEVICE COMPRISING A MAIN PART AND INCLUDING A BASE AND A REMOVABLE ELECTRODE

This application is the National Stage of International Application No. PCT/IB2015/053680, filed May 19, 2015, which claims the benefit of French Application No. 1454456, filed May 19, 2014, all the disclosures of which are incorporated by reference therein.

The invention relates to the technical field of devices intended to be fixed on a user's skin.

This in particular involves medical devices, such as pulse generators for electrostimulation.

It is recalled here that electrostimulation is a technique consisting of electrically stimulating nerves or muscles. Electrostimulation of the nerves (in particular transcutaneous electrical nerve stimulation, or TENS) in particular makes it possible to treat pain. Muscular electrostimulation (neuromuscular electrostimulation, or NMES) can be used for rehabilitation, muscle recovery or muscle strengthening purposes.

Electrostimulation devices comprise an electric pulse generator connected to cutaneous electrodes. The pulse generator makes it possible to send frequency- and intensity-calibrated electric pulses to a specific zone of the human body via cutaneous electrodes. In conventional devices, the pulse generator assumes the form of a bulky and rigid unit.

As an example, a pulse generator as described in the document by Mark Johnson, Transcutaneous Electrical Nerve Stimulation (Johnson, Mark I (October 2012), Transcutaneous Electrical Nerve Stimulation (TENS), eLS. John Wiley & Sons, Ltd.: Chichester) assumes the form of a bulky unit of about several tens of cubic centimeters and a thickness of about several centimeters.

This type of pulse generator is not practical to use. Indeed, it is a bulky object that is connected to cutaneous electrodes via relatively long electrical cables (typically more than 1 m long).

It has been proposed in the prior art to replace the conventional, bulky and rigid pulse generators with small pulse generators that can be worn directly by the user in the form of patches.

Such a thin and flexible pulse generator assuming the form of a patch is described in document U.S. Pat. No. 5,423,874.

In this patch, the power source of the battery type and the electronic components, which are discrete components, as well as integrated circuits making it possible to operate the pulse generator, are assembled on a flexible circuit.

The flexible circuit is encapsulated between an impermeable upper layer and an adhesive lower layer. The impermeable upper layer serves as a moisture barrier to protect the power source and the electronic components. The adhesive lower layer, which comprises two cutaneous electrodes, makes it possible to fasten the pulse generator on the skin.

This pulse generator is less bulky than the conventional pulse generators and makes it possible to greatly reduce the length of the power cables, or even to do away with these cables completely.

An electrostimulation device may include several electrodes, for example one or several fixed electrodes and one or several removable electrodes, or several removable electrodes.

The number and type of fixed electrodes are known for the device. This is not the case for the removable electrodes.

Yet an electrostimulation device may implement different programs, which may require specific types and numbers of removable electrodes.

Inasmuch as the removable electrodes are fastened by the user, it is necessary to determine what electrodes are connected to ensure that the chosen program can actually be launched.

Yet no known electrostimulation device provides technical solutions to this problem.

Furthermore, an electrostimulation device as described in document U.S. Pat. No. 5,423,874 is not versatile: the distance between electrodes is fixed and therefore cannot be adjusted by the patient based on his pathology and morphology.

The invention aims to offset these drawbacks by proposing a cutaneous medical device, in particular an electrostimulation device intended to be fixed on a user's skin, which makes it possible to recognize removable cutaneous electrodes and offers great freedom in adjusting the distance between electrodes.

Thus, the invention relates to a cutaneous medical device, in particular an electrostimulation device, comprising:

a main part containing an electricity source capable of generating an electric current and electronic components, to form part of an electric circuit, at least one removable cutaneous electrode including a plug, said electrode being intended to be in electrical contact with the user, at least one base positioned on a first face of the main part and able to be electrically connected with said removable cutaneous electrode.

According to the invention, the device comprises, in said at least one base, conductive means and, in said plug, a means for controlling the passage of the current between said conductive means, said conductive means and said control means forming an electric switch having a recognition function for said removable cutaneous electrode.

This recognition function includes at least two aspects: the possibility of detecting the type of cutaneous electrode connected to a given base and that of detecting the bases in which a cutaneous electrode has been connected.

Furthermore, the base includes at least one part having an electrical function and the plug includes a cylindrical part having an electrical function, the electrical connection between the base and the plug being provided by the electrical contact between the parts having an electrical function.

In a first alternative, an annular part has an electrical function.

In a second alternative, three parts arranged in a circle have an electrical function.

Preferably, these parts are mounted on a spring.

Preferably, the conductive means of the base comprise two assemblies that are fixed and electrically isolated from one another.

In a first example embodiment, the plug of said at least one removable electrode includes a protuberance having a height (h) such that the protuberance is able to come into contact with both fixed assemblies.

In a second example embodiment, the plug of said at least one removable electrode includes a protuberance having a height (h') such that it does not come into contact with the two fixed assemblies, when it is inserted into the cavity.

In one alternative, said conductive means of the base also comprise a deformable part placed above the two assemblies.

In a first example embodiment, the plug of said at least one removable electrode includes a protuberance having a height (h) such that the protuberance is able to deform said part when it is inserted in the cavity.

In a second example embodiment, the plug of said at least one removable electrode includes a protuberance having a height (h') such that no pressure is exerted by the protuberance on said part, when it is inserted into the cavity.

The device may comprise at least two bases and at least two removable cutaneous electrodes.

Advantageously, the device comprises at least two rigid zones and one flexible zone between two adjacent rigid zones.

Furthermore, the main part may include, on a second face, opposite the first, another cutaneous electrode intended to establish electrical contact with the user.

Preferably, the device comprises magnetic means both on the plug and the base.

Figure 1B:
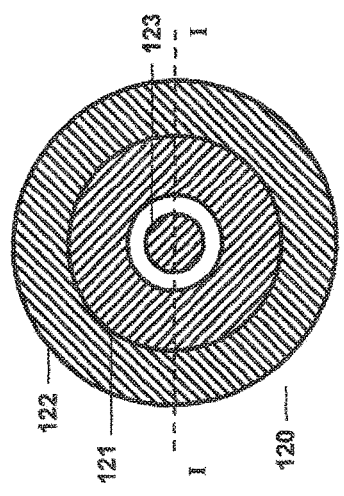
Figure 2:
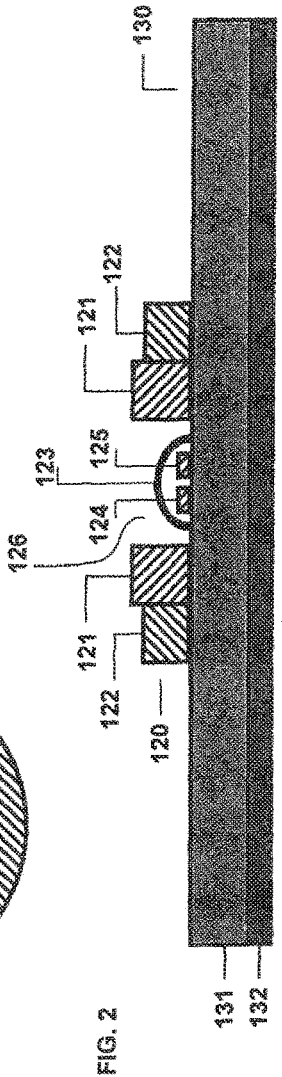
Figure 3A:
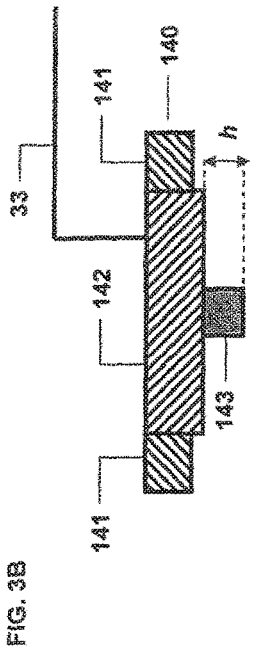
Figure 3B:
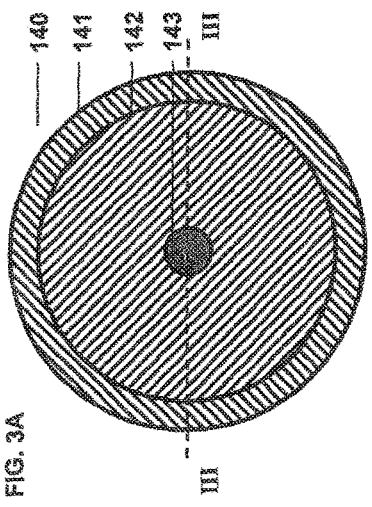
Figure 4A:
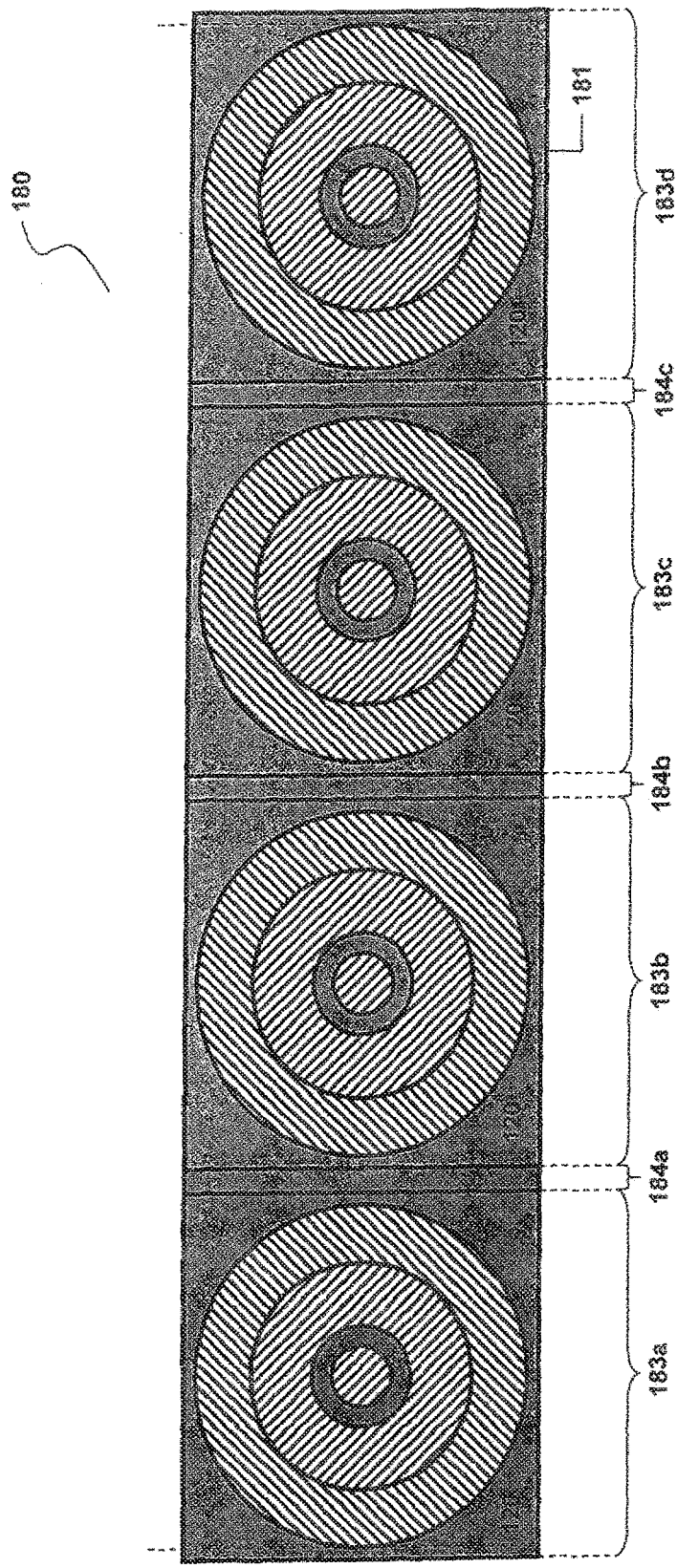
Figure 4B:
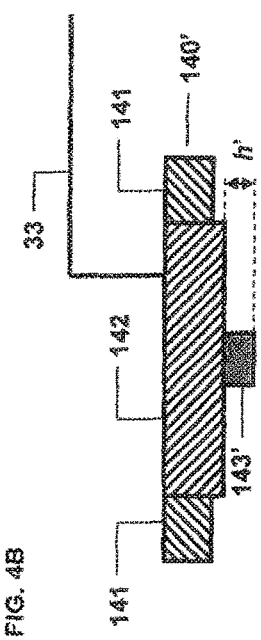
Figure 6:
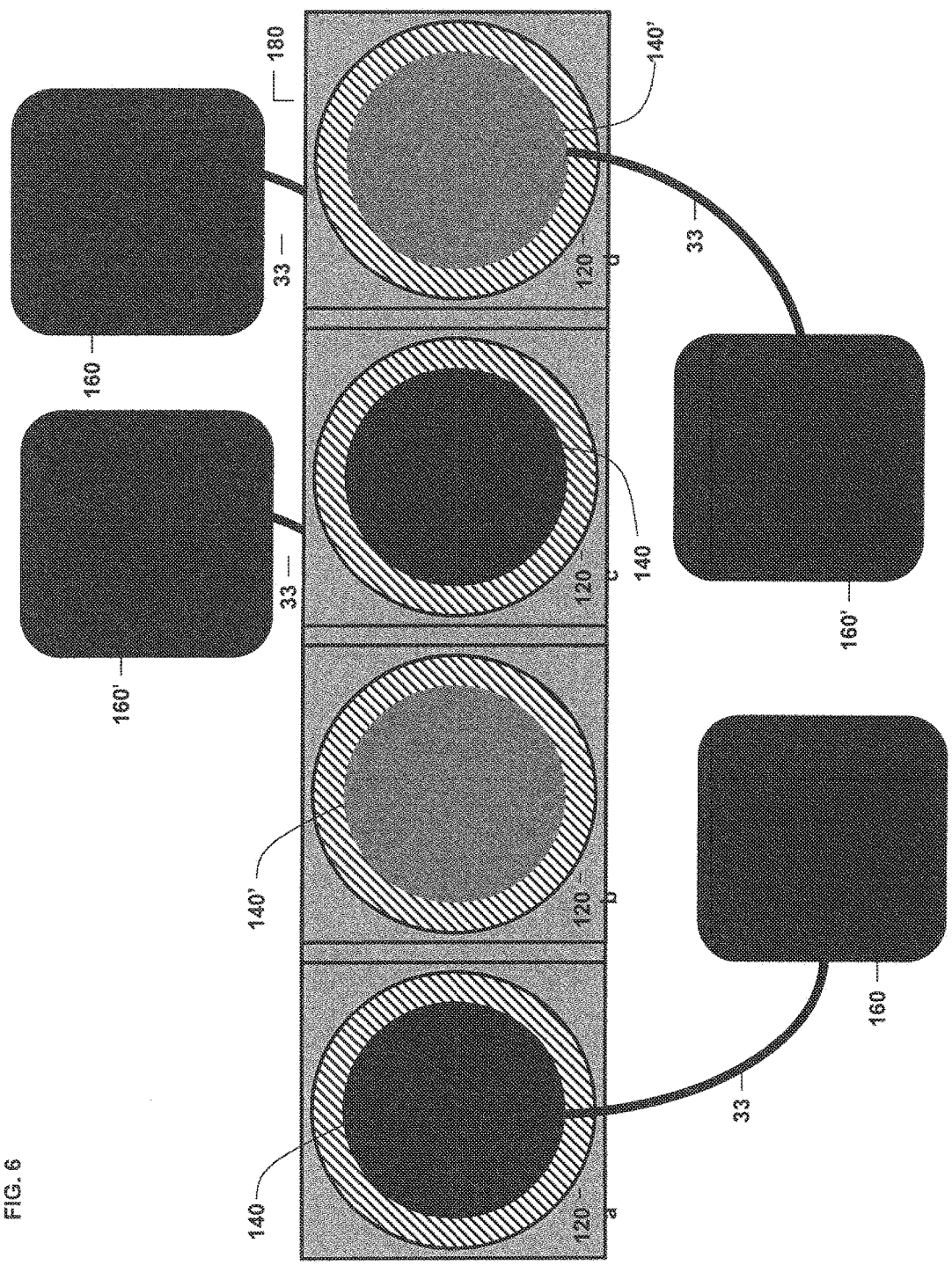

The invention will be better understood, and other aims, advantages and features thereof will appear more clearly, upon reading the following description done in reference to the appended drawings, in which:

FIG. 1 (1A-1B) comprises a top view (FIG. 1A) and a sectional view along line I-I (FIG. 1B) of an example of a female base, FIG. 2 is a sectional view of a cutaneous device comprising a base of the type illustrated in FIG. 1, FIG. 3 (3A-3B) comprises a bottom view (FIG. 3A) and a sectional view along line III-III (FIG. 3B) of a male plug adapted to the base illustrated in FIG. 1, FIG. 4 (4A-4B) comprises a top view (FIG. 4A) of a cutaneous device and a sectional view (FIG. 4B) of a male plug adapted to the cutaneous device illustrated in FIG. 4A, FIGS. 5 and 6 comprise top views of a device illustrated in FIG. 4 in two configurations for connecting removable cutaneous electrodes, FIG. 7 (7A-7B) comprises a top view (FIG. 7A) and a sectional view along line VII-VII (FIG. 7B) of an alternative embodiment of the base illustrated in FIG. 1, FIG. 8 is a top view of an alternative embodiment of the cutaneous device illustrated in FIG. 4A.

The elements shared by the different figures will be designated using the same references.

One embodiment of the device will now be described in reference to FIGS. 1 to 6.

FIG. 1A (top view) and FIG. 1B (sectional view along line II-II in FIG. 1A) show the base 120 of the electrical connector.

This is a base of the female type, i.e., including a hole 126.

The base 120 comprises two annular parts 121 and 122 centered around a same axis, the part 121 being situated inside the part 122. The part 121 has an electrical function. It for example involves a metal part. The part 122 has a magnetic function. It is for example a part made from ferrite, or aluminum-nickel-cobalt or samarium-cobalt or neodyme-iron-boron, which are magnetized materials.

At the center of the parts 121 and 122, a system is positioned in particular including an electrically conductive and deformable cup-shaped part 123 and two plate-shaped electrically conductive parts 124 and 125. The two parts 124 and 125 are electrically isolated from one another. These three parts can be made from metal.

Advantageously, only the inner face (turned toward the parts 124 and 125) of the cup 123 is conductive, its outer face being isolating.

FIG. 2 diagrammatically shows a device according to the invention, here a patch generating pulses for electrostimulation 130, incorporating the base 120.

The patch 130 comprises a main part 131 that in particular contains electronic components and an electrical power source.

On its lower face, it comprises hydrogel layers forming a first cutaneous electrode 132, intended to establish electrical contact with the user's skin.

The patch 130 comprises a base 120 on its upper face. It in particular makes it possible to connect the patch 130 to a second cutaneous electrode (not shown in the figures), via a plug 140 and a power cable 33 (shown in FIG. 3).

Reference is now made to FIGS. 3A (bottom view) and 3B (sectional view along line III-III in FIG. 3A), which show the male plug 140 of the electrical connector, intended to cooperate with the base 120 illustrated in FIG. 1.

The plug 140 comprises an annular part 141 and a cylindrical part 142 surrounded by the annular part 141 and forming its base.

The part 141 has a magnetic function. The part 142 has an electrical function and is connected to a power cable 33, which in turn is connected to a cutaneous electrode.

The plug 140 also comprises a central cylindrical part 143 with height h forming a protuberance, protruding relative to the parts 141 and 142.

Preferably, the part 141 is slightly withdrawn from the part 142, on the side of the protuberance 143.

The three parts 141, 142 and 143 are centered around a same axis.

The part 141 is for example a part made from ferrite, aluminum-nickel-cobalt or samarium-cobalt or made from neodyme-iron-boron, which are magnetized materials.

The part 142 is for example a metal part.

The part 143 is for example a polymer part.

The hole 126 of the base 120 is intended to accommodate the protuberance 143, which prevents accidental disconnection due to lateral forces, i.e., forces in the plane of the base 120.

The part 121 is intended to establish electrical contact with the part 142. The part 122 and the part 141 are intended to exert an attractive magnetic force on one another.

The height h of the protuberance 143 is sufficient to be able to exert pressure on the part 123, which leads to deforming it, when the plug 140 cooperates with the base 120. The part 123 thus deformed establishes electrical contact with the two parts 124 and 125.

The base 120 plays a dual role:
an electrical connector role: since it makes it possible to connect a device (for example, a patch generating electrostimulation pulses) to a cutaneous electrode, via the plug 140 and the power cable 33, more specifically owing to the electrical contact established between the part 142 of the plug 140 and the part 121 of the base 120;
a switch role: in cooperation with the plug 140, since the protuberance 143 of the plug 140 makes it possible to electrically connect the part 124 to the part 125, via the part 123 when the plug 140 is connected to the base 120, the two parts 124 and 125 otherwise being electrically isolated.

It will be understood that this term "switch" here does not correspond to an on/off switch making it possible to turn the electrostimulation device on and off. This on/off function is performed by other means that are not described here.

The parts 124 and 125 of the base are electrically connected via the protuberance 143 when the plug 140 is connected to the base. This therefore allows the electronic circuits of the patch 130 to recognize whether a removable electrode is connected to the patch depending on whether the switch is open or closed.

As an alternative, the deformable part 123 could be omitted. In this case, the part 143 forming a protuberance must include an electrically conductive end, electrically isolated from the part 142.

In this alternative, the parts 124 and 125 of the base are still electrically connected via the protuberance 143 when the plug 140 is connected to the base.

It should be noted that the deformable part 123 has the advantage of avoiding any risk of dirtying of the parts 124 and 125 during the lifetime of the device.

The electrical connector described in FIGS. 1 and 2 has the following advantages:
1) An accidental actuation of the switch, for example with the fingers, is relatively unlikely, since the parts 124 and 125 are positioned at the bottom of a cavity and not on the surface of the base.
2) Dirtying of the electrical contacts, for example by dust, is relatively unlikely, since the parts of the base having an electrical function are:
    a. either on the surface of the base, and therefore easy to clean (part 121),
    b. or at the bottom of a cavity, but protected from dirtying (the parts 124 and 125 are protected by the part 123).

FIG. 4A shows (top view) a patch generating pulses for electrostimulation 180.

The patch 180 comprises a main part 181 and in particular contains electronic components and at least one electrical power source.

On its upper face, the patch 180 comprises four bases 120 described in FIG. 1.

The patch 180 can be subdivided into seven zones:
    four rigid zones 183a, 183b, 183c, 183d: each of these four rigid zones comprises a base 120 and a set of components (electronic components, power sources, etc.). Preferably, in each of these four rigid zones, the base 120 is vertically aligned with the assembly of components, so as to cover it and therefore provide mechanical protection for it;
    three flexible zones 184a, 184b, 184c: comprising metal tracks making it possible to interconnect the components positioned in the rigid zones 183a, 183b, 183c, 183d.

Having an architecture made up of rigid zones (183a, 183b, 183c, 183d) connected by flexible zones (184a, 184b, 184c) makes it possible to ensure the flexibility and configurability of the patch 180 as a whole.

Within each of the four rigid zones 183a, 183b, 183c and 183d, combining the dual function of electrical connection means and mechanical protection means in a same element 120 makes it possible to gain compactness and thinness, while ensuring the reliability and robustness of the patch 180.

The bases 120 of the patch 180 can cooperate with two types of plugs: plugs of the type 140 described in FIG. 3 and plugs of the type 140' described in FIG. 4B.

The only difference between a plug 140 (FIG. 3) and a plug 140' (FIG. 4B) lies in the central cylindrical part forming a protuberance protruding relative to the parts 141 and 142.

In the plug 140', the part 143 with height h forming a protuberance is replaced by a part 143' with height h' forming a protuberance, with h'<h.

The connection of a plug 140 in a base 120 makes it possible both to:
    establish electrical contact between the part 142 of the plug 140 and the part 121 of the base 120 (electrical connector role),
    and electrically connect the part 124 to the part 125 (switch role while allowing current to flow between the two parts 124 and 125).

Conversely, the connection of a plug 140' in a base 120:
    makes it possible to establish electrical contact between the part 142 of the plug 140' and the part 121 of the base 120 (electrical connector role)
    but does not make it possible to electrically connect the part 124 to the part 125 (no switch role because the two parts 124 and 125 remain electrically isolated), since the height h' of the part 143' of the plug 140' is not sufficient to come into contact with the parts 124 and 125 or to deform the part 123 when it is provided.

It will therefore be understood that the electronic circuits of the patch 180 can thus automatically recognize the type of electrodes connected to the patch.

In particular, the electronic circuits of the patch 180 are capable of recognizing whether a base 120 is connected to a plug 140 or to a plug 140'. To that end, the electronic circuits of the patch 180 observe the state (open or closed) of the switch associated with the base 120 (i.e., the switch made up of the parts 124 and 125). For example, the electronic circuits of the patch 180 can comprise a microcontroller, a digital input of which is connected to a "pull-up" resistance in order to observe the state (open or closed) of the switch. The operating principle of a pull-up resistance is well known in the state of the art: the input of the microcontroller is in logic state 1 when the switch is open, and in logic state 0 when the switch is closed. Consequently, in this example, the input of the microcontroller is in logic state 1 when a plug 140' is connected to the base 120, and logic state 0 when the plug 140 is connected to the base 120.

In the first use of the patch 180, illustrated in FIG. 5, the user connects a single pair of cutaneous electrodes 160 to the patch 80.

Each of the two cutaneous electrodes 160 is connected to a power cable 33, which in turn is secured to a plug 140 that is connected to a base 120.

It is important to note that each of the two plugs 140 may be connected in any of the four bases 120, given that the four bases 120 are identical and can all cooperate with a plug 140.

In the case described in FIG. 5, the patch 180, which comprises four bases 120, is only connected to two cutaneous electrodes 160. Having a number of connecting means 120 (four in this example) greater than the number of plugs to be connected (two in this example) is advantageous, since this offers the user great positioning freedom of the cutaneous electrodes 160 on the body, for a given position of the patch 180.

Thus, the user has great positioning freedom of the cutaneous electrodes, and therefore great freedom to adjust the distance between the electrodes.

In a second use of the patch 180, illustrated in FIG. 6, the user connects two pairs of cutaneous electrodes 160, 160' to the patch 180 (i.e., four electrodes). This makes it possible to carry out two electrostimulation programs at the same time, each program corresponding to one of the pairs. These two programs can be different, and it is therefore important for the electronic circuits of the patch 180 to be able to recognize whether a cutaneous electrode belongs to the first pair (cutaneous electrode 160) or to the second pair (cutaneous electrode 160').

Each of the cutaneous electrodes 160 of the first pair is connected to a power cable 33, which in turn is secured to a plug 140 that is connected to a base 120. Each of the cutaneous electrodes 160' of the second pair is connected to a power cable 33, which in turn is secured to a plug 140' that is connected to a base 120.

The electronic circuits of the patch 180 can then recognize whether a cutaneous electrode belongs to the first pair or the second pair:
- a cutaneous electrode 160 of the first pair is secured to a plug 140, the connection of which to a base 120 causes the switch comprising the parts 124 and 125 to close,
- a cutaneous electrode 160' of the second pair is secured to a plug 140', the connection of which to a base 120 does not cause the closing of the switch comprising the parts 124 and 125.

It is important to note that each of the plugs 140 or 140' can be connected in any one of the four bases 120, given that the four bases 120 are identical and cannot cooperate with a plug 140 or 140'.

This offers the user great positioning freedom of the cutaneous electrodes 160 and 160' on the body, for a given position of the patch 180, and therefore great freedom in adjusting the distance between electrodes.

Furthermore, the recognition of the electrode can be done independently of the base in which it is connected.

Other applications of the switch function can be considered, in particular the automatic recognition of the bases in which a plug has been connected.

In the case, for example, of a patch having four identical bases, making it possible to connect the patch to a pair of cutaneous electrodes or two pairs of cutaneous electrodes, the bases in which a plug has been connected have their switch in a closed state, while the bases in which no plug has been connected have their switch in an open state. Thus, when the electronic circuit is turned on, it may detect the open or closed state of the switch integrated into a base to draw information therefrom on the connection or non-connection of an electrode in this base. The electronics of the patch can then distinguish the case of a normal situation (two plugs connected or four plugs connected) from the case of an abnormal situation (no plug connected, or a single plug connected, or three plugs connected).

In the case of an abnormal situation, the patch blocks the launch of electrostimulation programs in order to protect the user.

In the case of a normal situation where two plugs are connected (i.e., where a single pair of cutaneous electrodes is connected), the patch authorizes the launch of electrostimulation programs on this pair of cutaneous electrodes. However, the patch does not power on the two bases left unoccupied, still in order to protect the user.

In the case of a normal situation where four plugs are connected (i.e., where two pairs of cutaneous electrodes are connected), the patch authorizes the launch of electrostimulation programs on both pairs of cutaneous electrodes.

An alternative of the base 120 is described in reference to FIG. 7.

FIG. 7A (top view) and FIG. 7B (sectional view along line VII-VII in FIG. 7A) show a base 220, which is an alternative of the base 120.

In the base 220, three parts 221a, 221b and 221c replace the part 121 of the base 120. These three parts 221a, 221b and 221c are arranged in a concentric circle with the annular part 122 and a smaller diameter. The part 123 is situated inside the circle.

Like the part 121 of the base 120, the three parts 221a, 221b and 221c of the base 220 have an electrical function, and are intended to establish electrical contact with the part 142 of a plug 140 or 140'.

The three parts 221a, 221b and 221c are advantageously mounted on a spring, which allows a greater tolerance on the dimensions of the different parts making up the base and the plugs.

The invention is not, however, limited to this embodiment. In practice, it suffices to provide only one of these parts. Furthermore, more than three parts could be provided.

An alternative of the pulse-generating patch 180 is described in reference to FIG. 8, which shows a pulse-generating patch 230.

The patch 230 comprises a main part 231 and in particular contains electronic components and at least one electrical power source.

The patch 230 comprises, on its upper face, four bases 120 described in FIG. 1.

The patch 230 can be subdivided into five zones:
- three rigid zones 233a, 233b, 233c: each of these three rigid zones comprises a set of components (electronic components, power sources, etc.). The zones 233a and 233c additionally each comprise two bases 120. Preferably, in the zones 233a and 233c, the bases are vertically aligned with the components, so as to cover them and therefore provide mechanical protection for them;
- two flexible zones 234a, 234b: comprising metal tracks making it possible to interconnect the components positioned in the rigid zones 233a, 233b, 233c.

Relative to the patch 180, the patch 230 is therefore shorter, which is advantageous for positioning on certain zones of the body (for example, the forearms).

The reference signs inserted after the technical features appearing in the claims are intended solely to facilitate the understanding thereof and may not limit their scope.

The invention claimed is:

1. A cutaneous medical device, comprising:
   a main part containing:
      an electricity source configured to generate an electric current, and
      electronic components at least partially forming an electric circuit;
   at least one removable cutaneous electrode including a plug, the at least one removable cutaneous electrode being configured to be in electrical contact with a user; and
   at least one base positioned on a first face of the main part and capable of being electrically connected with the at least one removable cutaneous electrode,
   wherein the at least one base comprises conductive parts and the plug comprises means for controlling the passage of the current between the conductive parts, wherein the conductive parts are at least in part housed by a common conductive cup, and wherein the conductive parts and the control means form an electric switch having a recognition function for the removable cutaneous electrode by electrically connecting the conductive parts by deforming the conductive cup.

2. The device of claim 1, wherein the at least one base includes at least one part having an electrical function and the plug includes a cylindrical part having an electrical function, the electrical connection between the at least one base and the plug being provided by the electrical contact between the at least one part having the electrical function and the cylindrical part.

3. The device of claim 2, wherein an annular part has an electrical function.

4. The device of claim 2, wherein the at least one base comprises three parts arranged in a circle, and wherein the three parts have an electrical function.

5. The device of claim 4, wherein the three parts of the at least one base are individually mounted on their corresponding springs.

6. The device of claim 1, wherein the conductive parts of the at least one base comprise two assemblies that are fixed and electrically isolated from one another.

7. The device of claim 6, wherein the plug of the at least one removable electrode includes a protuberance having a height such that the protuberance is able to come into contact with both fixed assemblies.

8. The device of claim 6, wherein the plug of the at least one removable electrode includes a protuberance having a height such that it does not come into contact with the two fixed assemblies when it is inserted into a cavity that houses the two fixed assemblies.

9. The device of claim 6, wherein the conductive parts of the base also comprise a deformable part placed above the two assemblies.

10. The device of claim 8, wherein the plug of the at least one removable electrode includes a protuberance having a height such that the protuberance is able to deform the part when it is inserted into the cavity.

11. The device of claim 8, wherein the plug of the at least one removable electrode includes a protuberance having a height such that no pressure is exerted by the protuberance on the part when it is inserted into the cavity.

12. The device of claim 1, comprising at least two bases and at least two removable cutaneous electrodes.

13. The device of claim 1, wherein the main part includes, on a second face, opposite the first, another cutaneous electrode intended to establish electrical contact with the user.

14. The device of claim 1, wherein the plug and the base are magnetic.

15. The device of claim 1, comprising four rigid zones and three flexible regions between two adjacent rigid zones.

16. The device of claim 1, comprising three rigid zones and two flexible regions between two adjacent rigid zones.

* * * * *